United States Patent
Brahmachari et al.

(10) Patent No.: US 7,825,230 B2
(45) Date of Patent: Nov. 2, 2010

(54) HUMAN MICRORNA TARGETS IN HIV GENOME AND A METHOD OF IDENTIFICATION THEREOF

(75) Inventors: Samir Kumar Brahmachari, Delhi (IN); Manoj Hariharan, Delhi (IN); Vinod Scaria, Delhi (IN); Beena Pillai, Delhi (IN)

(73) Assignee: Council of Scientific & Industrial Research, New Delhi (IN)

( * ) Notice: Subject to any disclaimer, the term of this patent is extended or adjusted under 35 U.S.C. 154(b) by 0 days.

(21) Appl. No.: 11/545,280

(22) Filed: Oct. 10, 2006

(65) Prior Publication Data
US 2007/0087335 A1   Apr. 19, 2007

(30) Foreign Application Priority Data
Oct. 10, 2005   (IN)   .................. 2729/DEL/2005

(51) Int. Cl.
*C07H 21/04*   (2006.01)
(52) U.S. Cl. ..................... 536/23.1; 536/24.5
(58) Field of Classification Search ............ None
See application file for complete search history.

(56) References Cited

U.S. PATENT DOCUMENTS 5,474,796 A * 12/1995 Brennan ............... 427/2.13

OTHER PUBLICATIONS

Lagos-Quintana et al (Science 294: 853-858, 2001).*
Dostie et al (RNA 9(2): 180-186, 2003).*
Ratner et al (Nature 313(6000): 277-284, 1985).*
Gen Bank K03455 (2002).*
Buck et al (Biotechniques 27: 528-536, 1999).*
Svanholm et al (Scand. J. Immunol. 46: 298-303, 1997).*
GenBank Accession AF324493, 2001.*

* cited by examiner

*Primary Examiner*—Richard Schnizer
(74) *Attorney, Agent, or Firm*—Harness Dickey & Pierce, PLC (57) ABSTRACT

The present invention relates to human microRNA targets in HIV genome and a method of identification thereof. Using multiple software targets to six human microRNAs [miRNAs] were discovered in the net, vpr, env, and I vif genes. The miRNAs were identified as hsa-miR-29a, hsa-miR-29b, hsa-miR-29c, hsa-mir-149, hsa-mir-324-5p, hsa-mir-378. These miRNAs or its homologues can be used as therapeutics against HIV infection. The invention further relates to a novel strategy to target genes of HIV-1 by human microRNAs, or its homologues, to inactivate or block HIV activity. The computational approach towards identification of human miRNA targets in the HIV genome and the variation in the microRNA levels was further validated experimentally.

2 Claims, 4 Drawing Sheets

SEQUENCE LISTING

<160> NUMBER OF SEQ ID NOS: 21

<210> SEQ ID NO 1
<211> LENGTH: 22
<212> TYPE: DNA
<213> ORGANISM: Human immunodeficiency virus type 1

<400> SEQUENCE: 1
cactgacctt tggatggtgc ta                                        22

<210> SEQ ID NO 2
<211> LENGTH: 24
<212> TYPE: DNA
<213> ORGANISM: Human immunodeficiency virus type 1

<400> SEQUENCE: 2
tccactgacc tttggatggt gcta                                      24

<210> SEQ ID NO 3
<211> LENGTH: 21
<212> TYPE: DNA
<213> ORGANISM: Human immunodeficiency virus type 1

<400> SEQUENCE: 3
actgaccttt ggatggtgct a                                         21

<210> SEQ ID NO 4
<211> LENGTH: 23
<212> TYPE: DNA
<213> ORGANISM: Human immunodeficiency virus type 1

<400> SEQUENCE: 4
ggagagcaag aaatggagcc agt                                       23

<210> SEQ ID NO 5
<211> LENGTH: 24
<212> TYPE: DNA
<213> ORGANISM: Human immunodeficiency virus type 1

<400> SEQUENCE: 5
gtacacatcc cactagggga tgct                                      24

<210> SEQ ID NO 6
<211> LENGTH: 21
<212> TYPE: DNA
<213> ORGANISM: Human immunodeficiency virus type 1

<400> SEQUENCE: 6
ctacagtatt ggagtcagga a                                         21

<210> SEQ ID NO 7
<211> LENGTH: 21
<212> TYPE: RNA
<213> ORGANISM: Homo sapiens
<220> FEATURE:
<221> NAME/KEY: misc_feature
<222> LOCATION: (1)..(21)
<223> OTHER INFORMATION: 3' - 5'

<400> SEQUENCE: 7
uuggcuaaag ucuaccacga u                                         21

```
<210> SEQ ID NO 8
<211> LENGTH: 23
<212> TYPE: RNA
<213> ORGANISM: Homo sapiens
<220> FEATURE:
<221> NAME/KEY: misc_feature
<222> LOCATION: (1)..(23)
<223> OTHER INFORMATION: 3' - 5'

<400> SEQUENCE: 8
uugugacuaa aguuuaccac gau                                              23

<210> SEQ ID NO 9
<211> LENGTH: 20
<212> TYPE: RNA
<213> ORGANISM: Homo sapiens
<220> FEATURE:
<221> NAME/KEY: misc_feature
<222> LOCATION: (1)..(20)
<223> OTHER INFORMATION: 3' - 5'

<400> SEQUENCE: 9
uggcuaaagu uuaccacgau                                                  20

<210> SEQ ID NO 10
<211> LENGTH: 22
<212> TYPE: RNA
<213> ORGANISM: Homo sapiens
<220> FEATURE:
<221> NAME/KEY: misc_feature
<222> LOCATION: (1)..(22)
<223> OTHER INFORMATION: 3' - 5'

<400> SEQUENCE: 10
ccucacuucu gugccucggu cu                                               22

<210> SEQ ID NO 11
<211> LENGTH: 23
<212> TYPE: RNA
<213> ORGANISM: Homo sapiens
<220> FEATURE:
<221> NAME/KEY: misc_feature
<222> LOCATION: (1)..(23)
<223> OTHER INFORMATION: 3' - 5'

<400> SEQUENCE: 11
ugugguuacg ggaucccua cgc                                               23

<210> SEQ ID NO 12
<211> LENGTH: 22
<212> TYPE: RNA
<213> ORGANISM: Homo sapiens
<220> FEATURE:
<221> NAME/KEY: misc_feature
<222> LOCATION: (1)..(22)
<223> OTHER INFORMATION: 3' - 5'

<400> SEQUENCE: 12
uguguccugg accucagucc uc                                               22

<210> SEQ ID NO 13
<211> LENGTH: 14
<212> TYPE: DNA
<213> ORGANISM: Artificial Sequence
<220> FEATURE:
<223> OTHER INFORMATION: 5'-3' hsa-miR-29a primer

<400> SEQUENCE: 13
```

```
aaccgatttc agat                                                        14

<210> SEQ ID NO 14
<211> LENGTH: 16
<212> TYPE: DNA
<213> ORGANISM: Artificial Sequence
<220> FEATURE:
<223> OTHER INFORMATION: 5'-3' hsa-miR-29b primer

<400> SEQUENCE: 14
cactgatttc aaatgg                                                      16

<210> SEQ ID NO 15
<211> LENGTH: 16
<212> TYPE: DNA
<213> ORGANISM: Artificial Sequence
<220> FEATURE:
<223> OTHER INFORMATION: 5'-3' hsa-miR-29c primer

<400> SEQUENCE: 15
ccgatttcaa atggtg                                                      16

<210> SEQ ID NO 16
<211> LENGTH: 22
<212> TYPE: RNA
<213> ORGANISM: Human immunodeficiency virus type 1

<400> SEQUENCE: 16
cacugaccuu uggauggugc ua                                               22

<210> SEQ ID NO 17
<211> LENGTH: 24
<212> TYPE: RNA
<213> ORGANISM: Human immunodeficiency virus type 1

<400> SEQUENCE: 17
uccacugacc uuuggauggu gcua                                             24

<210> SEQ ID NO 18
<211> LENGTH: 24
<212> TYPE: RNA
<213> ORGANISM: Human immunodeficiency virus type 1

<400> SEQUENCE: 18
uccacugacc uuuggauggu gcua                                             24

<210> SEQ ID NO 19
<211> LENGTH: 23
<212> TYPE: RNA
<213> ORGANISM: Human immunodeficiency virus type 1

<400> SEQUENCE: 19
ggagagcaag aaauggagcc agu                                              23

<210> SEQ ID NO 20
<211> LENGTH: 24
<212> TYPE: RNA
<213> ORGANISM: Human immunodeficiency virus type 1

<400> SEQUENCE: 20
guacacaucc cacuagggga ugcu                                             24

<210> SEQ ID NO 21
<211> LENGTH: 21
```

-continued

```
<212> TYPE: RNA
<213> ORGANISM: Human immunodeficiency virus type 1

<400> SEQUENCE: 21
cuacaguauu ggagucagga a                                              21
```

HUMAN MICRORNA TARGETS IN HIV GENOME AND A METHOD OF IDENTIFICATION THEREOF

FIELD OF INVENTION

The present invention relates to human microRNA targets in HIV genome and a method of identification thereof. It specifically relates to a novel strategy to target genes of HIV-1 by human microRNAs, or its homologues, to inactivate or block HIV activity.

BACKGROUND OF THE INVENTION

Human immunodeficiency virus-1 (HIV-1) has been identified as the etiological agent responsible for acquired immune deficiency syndrome (AIDS), a fatal condition that arises by the invasion of the virus on various cells of the human immune system, mainly the T-cells. HIV is a member of the lentivirus, a subfamily of retrovirus, which have a single stranded ribonucleic acid (RNA) as the genetic material. The virus has the ability to integrate its genetic information into the genome of the host cell thereby blocking normal genetic flow of information in the cell. The virus then takes over the cellular machinery and replicates itself by synthesizing its own proteins and packaging the genetic material. Another feature of HIV infection is that the virus does not keep replicating itself all the time. There are "window periods" after infection, during which replication is not observed. This is regarded as a silent phase where the effect of the infection during which immune deficiency is not detected. A critical aspect of HIV infection is that, it infects and invades cells of the immune system, resulting in break-down of the body's immune system and rendering the patient susceptible to opportunistic infections and conditions like neoplasms which arise due to immune system inactivation. HIV-1 is cytopathic for T4 lymphocytes, cells of the immune system that express the cell surface differentiation antigen CD4. In addition to CD4+ T cells, the host range of HIV includes cells of the mononuclear phagocytic lineage, including blood monocytes, tissue macrophages, Langerhans cells of the skin, and dendritic reticulum cells within lymph nodes.

Worldwide, researchers have been engaged in studies to develop effective therapeutic antiviral agents and vaccines against this deadly virus. Currently accepted strategies are mainly based on non-nucleotide analog inhibitors of reverse transcriptase, such as Nevirapine (BI-RG-587), TIBO (R82913), pyrinodes (such as R-697,661 and L-696,227), bis(heteroary) piperazines (BHAPs, such as U-87201E and U-90,152), atevirdine mesylate (ATV) and R-89431; HIV protease inhibitors, include substrate analogs and non-analogs, such as Ro 31-8959, A-77003 and A-80987; HIV Tat protein inhibitors, such as Ro 5-3335 and Ro 27-7429; blockers of viral entry into cells, such as soluble CD4 protein (sCD4), and chimeric sCD4 derivatives, such as CD4-lgG and CD4-PE40; blockers of HIV RNaseH activity, such as the AZT derivative azidothymidine monophosphate; drugs that alter the intracellular milieu to create conditions less favorable for viral replication, such as the free-radical scavengers and glutathione-level restoring drugs (N-acetylcysteine and similar drugs), and thalidomine (which seems to lower blood TNF-.alpha. levels). Efforts have also focused on manipulation of the immune system and viral replication with naturally-occurring cytokines and lymphokines, or other agonists or antagonists of these systems. One of the drugs most frequently used is azidothimidine (AZT). Antiviral therapies with pharmaceuticals that inhibit the replication of HIV have been found to decrease plasma virus to undetectable levels.

Combination antiviral HIV therapy with Protease Inhibitors (PI) and Reverse Transcriptase (RT) inhibitors has provided Highly Active Antiviral Therapy (HAART). HAART results in the rapid cessation of viral replication and the decline of plasma virus to undetectable levels within 4-8 weeks. More recently, short interfering RNA (siRNA) has been tried against HIV infection. The property of siRNA that is made use here is that the binding of these small RNAs to mRNA would result in the cleavage of the mRNA which consequently inhibits protein synthesis.

Even before siRNA-based therapy has reached the clinical trial stage for use as an anti-HIV mechanism, probability of failure exist owing to the fact that exact complementarity is a necessity for siRNA activity. HIV is observed to constantly mutate its genome and this would result in rendering the siRNA-mediated inhibition a failure. However, miRNAs may offer a more effective alternative since they require incomplete complementarity.

Recently it was shown that human miRNAs can down regulate Hepatitis C Virus (HCV) and Primate Foamy Virus-1 (PFV-1) mRNA. The inventors have observed that human microRNAs hsa-mir-29a, hsa-mir-29b and hsa-mir-29c, which were predicted by all the programs, exclusively target the nef gene of HIV-1. Viral genes like tat and the gene coding for reverse transcriptase, as well as genes of host origin required for viral transcription have previously been targeted using siRNAs. In the present study, the inventors have shown that human microRNAs may target HIV-1 genes. These miRNAs have highly conserved targets in HIV-1 and related lade sequences. They are expressed in T-cells, the natural site of infection by HIV-1 infection and their expression level may vary between individuals. In summary, our study implies that human miRNAs have the potential to affect expression of HIV-1 genes and may in future be used to develop therapeutic approaches to inhibit HIV-1.

Drawbacks of Existing Therapies

Although AZT has proved effective in many cases, lowering mortality rates, the virus develops resistance to AZT, and the drug has significant and adverse side effects.

In most instances, HAART alone does not lead to complete immune recovery. Another drawback of HAART is that HIV develops resistance to it. Moreover, it now appears that many individuals may not be able to take HAART indefinitely, due to serious long-term side effects. As many as 40%-60% of patients who have received HAART for greater than one year have developed symptoms of Cushing's Syndrome, with hyperglycemia, hyperlipidemia, centipetal fat distribution, and peripheral muscle wasting.

Even before siRNA-based therapy has reached the clinical trial stage for use as an anti-HIV mechanism, probability of failure exist owing to the fact that exact complementarity is a necessity for siRNA activity. HIV is observed to constantly mutate its genome and this would result in rendering the siRNA-mediated protein inhibition a failure.

Accordingly, there is a need for new safe and efficient therapeutic and preventive methods for HIV-infections. The invention addresses this need in the field.

OBJECT OF THE INVENTION

The main object of the invention is thus to provide a novel strategy to target genes of HIV-1 by human microRNAs, or its homologues, to inactivate or block HIV activity and obviate the drawbacks mentioned above.

Yet another objective is to use synthetic miRNA, based on modified nucleosides, as therapeutic to prevent or inhibit the progression of disease.

Still another object is to provide miRNA expression variation as a genetic basis for long term progression of HIV infection.

Another object is to provide miRNA mediated inhibition of protein synthesis in HIV-1.

Still another object of the invention is to use variation of expression of human miRNAs as a prognostic genetic bio-marker in HIV-1 infection.

Novelty of Invention
  a novel strategy to target HIV genes by human microRNA
  use of microRNA to inactivate or block HIV activity
  provides a method to repress synthesis of proteins of HIV-1 use of human microRNA expression variation as a prognostic marker in HIV-1 infection method to predict targets for HIV-1 genes with microRNAs use and synthesis of miRNA, based on modified nucleosides, to block HIV-1 proteins

DRAWINGS

FIG. 1 shows positions of the five microRNA targets on the HIV-1 genome.

FIG. 2: Scheme 1: Protocol for Luciferase assay

FIG. 3: Effect of hsa-miR-29a on nef gene using Anti-miR 29a

FIG. 4: Effect of hsa-miR-29b on nef gene using Anti-miR 29b

FIG. 5: Effect of hsa-miR-29c on nef gene using Anti-miR 29c

FIG. 6: Expression of miR 29a, b, c

SUMMARY OF THE INVENTION

The invention relates to the identification of targets to human encoded microRNA on the HIV genome and a method of targeting HIV genes with human microRNAs. The invention provides drug targets in HIV genome based on microRNAs for HIV activity inhibition.

MicroRNAs are short RNA molecules which have the ability to repress protein synthesis by binding to messenger RNAs. In the present invention the applicants have screened HIV-1 reference genome computationally using human microRNAs for identifying targets for HIV activity inhibition. The invention also provides microRNA expression variation as a genetic basis for long term progression of HIV-1 infection.

Accordingly, the present invention relates to the targets for human microRNAs in HIV genome and a method of identification thereof.

The invention provides targets of six human microRNAs in HIV-1 reference genome comprising nucleotide stretches of SEQ ID Nos. 1 to 6e invention specifically provides microRNA targets for the HIV genome wherein hsa-miR-29a, hsa-miR-29b and hsa-miR-29c target the nucleotide stretches of SEQ ID NOS 1,2 and 3 in the nef gene.

The invention further provides microRNA targets for HIV genome wherein hsa-mir-149, hsa-mir-324-5p and hsa-mir-378 target the nucleotide stretches of SEQ ID NOS 4, 5 and 6 in the vpr, vif and env genes respectively.

The invention also discloses a method of targeting HIV genes with human miRNAs which comprises:

Downloading and shuffling computationally the whole genome HIV sequence from publicly available database.

Predicting computationally, the targets for microRNAs in the shuffled HIV genome sequences and computing the cut-off.

Deriving consensus predictions for microRNA-target pairs (which have scores >the cutoff of step 3) for six human microRNA.

Mapping computationally the human microRNA targets in HIV-1 genome.

Another aspect of the invention is to provide targets for miRNA sequences (SEQ ID NOS: 1 to 6) in 12 other related HIV-1 clades which represent the various subtypes of HIV-1.

Still another aspect of the invention is to provide use of miRNA expression variation as a genetic basis for long term progression of HIV infection.

In an embodiment to the invention, the software programs used for computational predictions consist of software available in public domain, viz., RNAhybrid, miRanda, DIANA-micro-T and microInspector.

In another embodiment to the invention, publicly available software—ShuffleSeq—was used for shuffling downloaded HIV genome to minimize error due to sequence compositional bias.

The parameters used for prediction of targets comprised of sequence complimentarity, minimum free energy of the duplex and continuous seed complementarity towards the 5' end of the microRNA.

Still another aspect of the invention is the use of miRNA or its homologues as therapeutics to prevent or inhibit the progression of disease by microRNA mediated inhibition of protein synthesis in HIV-1.

Yet another aspect of the invention is the use of synthetic oligomers that can bind as microRNA which can inhibit or repress protein synthesis in HIV-1. The ribonucleosides of the oligomer can be modified using strategies like Locked Nucleic Acid (LNA) or 2'-O-methyl RNA (OMe) resulting in better stability and binding to the target mRNA strand, thus enabling the repression of the HIV-1 proteins.

Still another aspect of the invention is the association of miRNA expression levels with disease progression and use of variation of expression of human miRNAs as a prognostic genetic bio-marker in HIV-1 infection.

DETAILED DESCRIPTION OF THE PRESENT INVENTION

Data Retrieval

The human microRNA mature sequences were downloaded from The miRNA Registry. For querying probable targets in the HIV-1 genome, the RefSeq validated HIV-1 reference sequence, obtained from the National Center for Biotechnology Information (NCBI) website and was used along with 12 representative related strain sequences, as identified by the International Committee on Taxonomy of Viruses (ICTV). The Glade sequences were obtained from the ICTV database.

Prediction of miRNA Targets in HIV-1

The applicants used four well-established microRNA target prediction softwares—miRanda, RNAhybrid, MicroInspector and DIANA-MicroT to predict targets for the 211 human miRNAs obtained from The microRNA Registry, in the HIV-1 reference sequence and the 12 representative lade sequences. HIV-1 targets to human microRNAs were initially predicted using miRanda with default parameters (Gap Open Penalty: −8.0; Gap Extend: −2.0; Score Threshold: 50.0; Energy Threshold: −20.0 kcal/mol; Scaling Parameter: 2.0). In order to increase the stringency, a cut-off score was derived above which the miRNA-target pairs were selected. A cut-off score of 120 was derived by running the same program on a shuffled sequence of HIV-1 reference strain with the same set of miRNAs. HIV-1 genome sequence was shuffled using the EMBOSS2 program shuffleseq. This enabled filtering of probable false positive hits and selection of the most probable and high-scoring values. These shortlisted HIV-1 targets to human microRNAs were also found to be highly probable targets on the other prediction software. Prior to running the RNAhybrid program, the RNAcalibrate module was used to derive the xi and theta values for calculation of Extreme Value Distribution. The xi—theta values thus obtained were included as one of the parameters while using RNAhybrid for target prediction. This minimizes the base composition bias. Also, the helix parameters were set to include maximum continuous complementarity towards the 5' end of the miRNA. It was observed that out of the several probable targets predicted by RNAhybrid, the six filtered pairs from miRanda had the lowest minimum free energy. Similar observations were made when the other two software were employed with default parameters, viz., minimum free energy of −20. Similarly the targets were predicted on the representative lade sequences also using miRanda. The target regions were mapped to the genomes of the 12 HIV clades. The target sites for the respective miRNAs were aligned using TCoffee server.

Validation of miRNA Targets in HIV Genome

The target of miRNA 29a, 29b and 29c found in the nef gene of HIV genome was further validated by experimental means. The validation was carried out in a cell culture model employing HeLa cells. Primer extension based methods described below were used to ensure that HeLa cells express the miRNAs being tested. A vector with the firefly luciferase gene under the control of a constitutive promoter was used to monitor the activity of the miRNA. Cultured HeLa cells were transfected with various constructs bearing reporter gene which carried testable target regions in their 3'Untranslated regions. Subsequently, the reporter gene activity was monitored using enzymatic assays. The expression level of the reporter would be expected to get downregulated if the cellular miRNA binds to the 3'UTR and results in translational block of the target HIV-1 gene (scheme 1). Furthermore, specificity of the interaction was validated by introducing an anti-miRNA, complimentary in sequence to the miRNA being tested. The DNA oligonucleotide which acts as an anti-miRNA molecule interferes in the action of the miRNA and restores the reporter gene activity.

Figure 1:
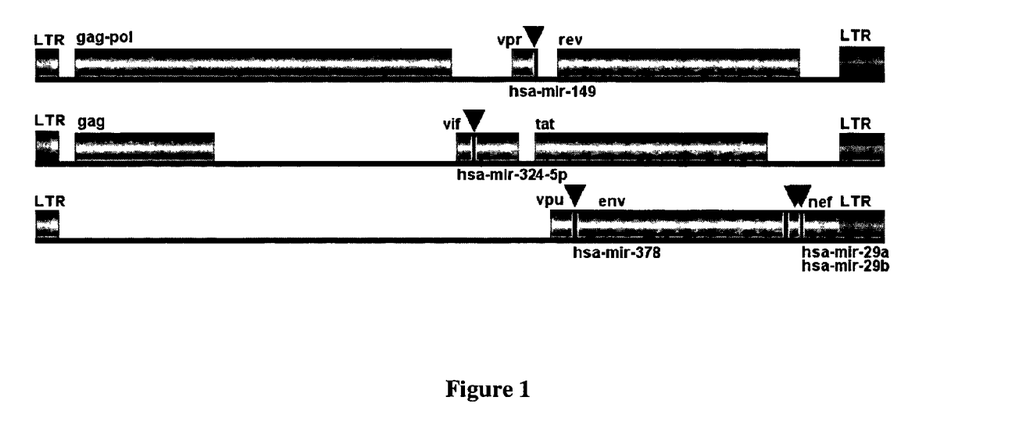
Figure 2:
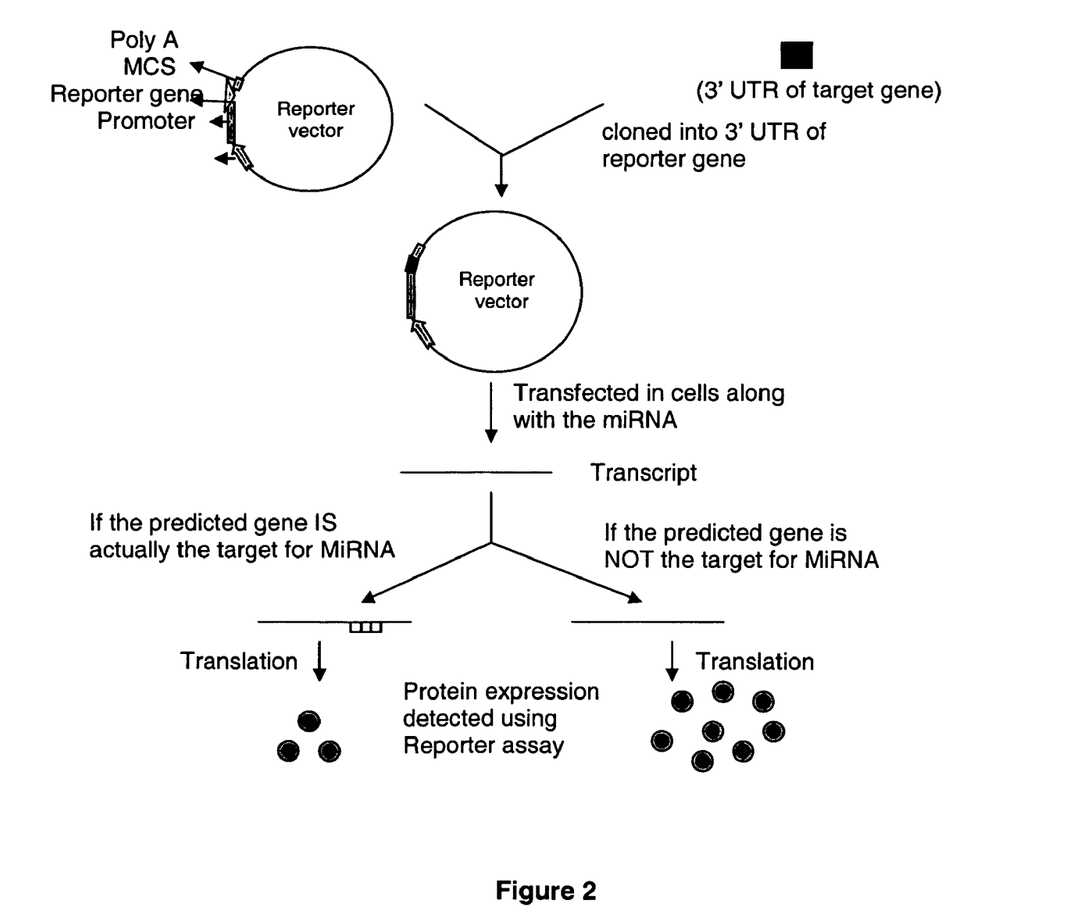
Figure 3:
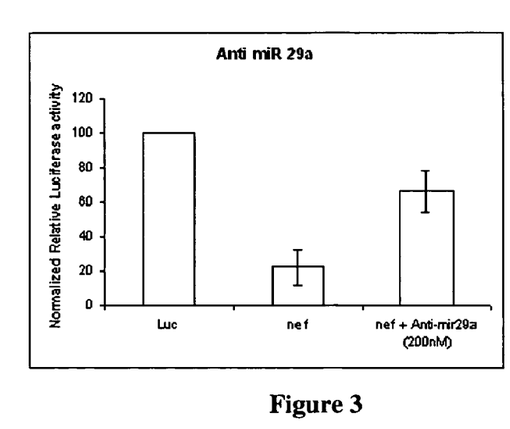

Targets for 29a, 29b and 29c within the nef gene showed dependence on the miRNA in the Hela cell since expression levels from the clone carrying the target region were downregulated compared to the expression from the vector without the target regions. Anti-miRNA against 29a and 29b could partially restore the reporter activity (FIG. 2 and FIG. 3). However an unrelated anti-miRNA i.e. anti-mir 149 had no such effect proving that this is not a non-specific effect of DNA oligos.

Expression Profile Analysis of miRNA

Microarray based expression data was retrieved from ArrayExpress database. The raw intensity data for each experiment was log transformed and then used for the calculation of Z scores. Z scores were calculated by subtracting the overall average gene intensity (within a single experiment) from the raw intensity data for each gene, and dividing the result by the standard deviation of all of the measured intensities, according to the formula: Z score=(Intensity G-mean intensity G1 ... Gn)/SDG1 ... Gn.

Figure 4:
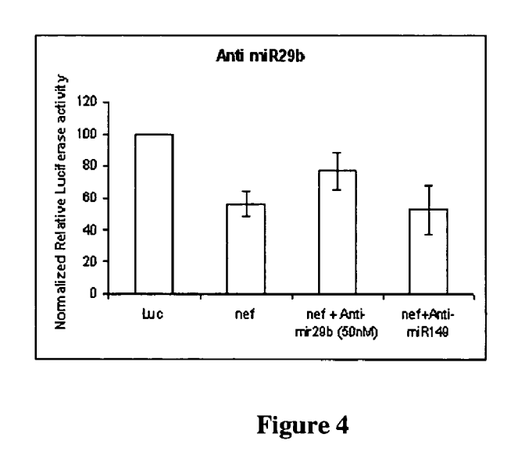
Figure 5:
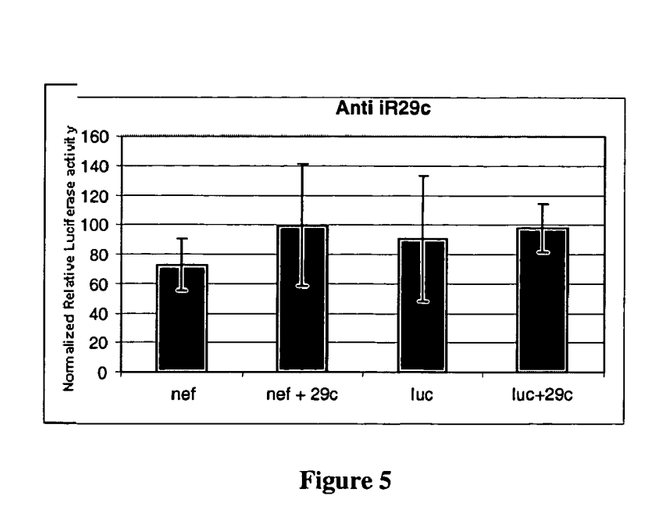
Figure 6:
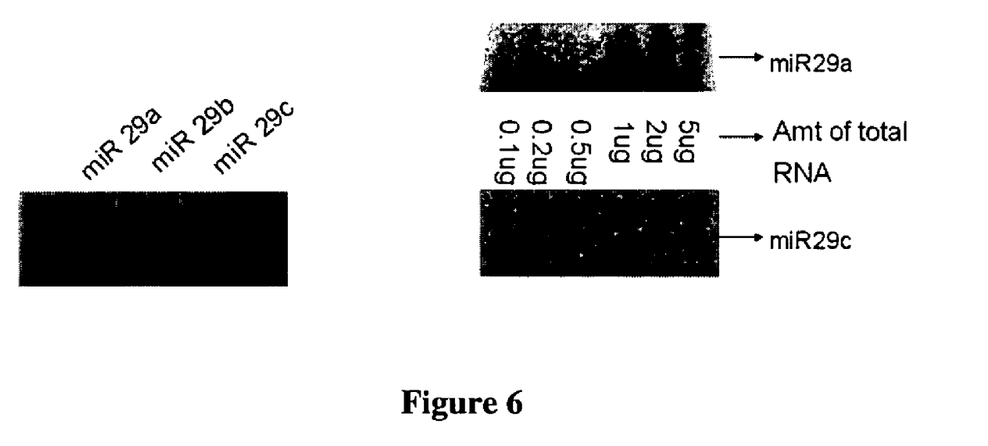

We adopted a consensus target prediction approach using multiple miRNA target prediction softwares, vis, miRanda, RNAhybrid, DIANA-MicroT and MicroInspector. Firstly, the inventors identified highly probable targets to six human miRNAs in the HIV-1 genome using the miRNA target prediction software miRanda which takes into account continuous base complementarity at the 5' end of the microRNA and minimum free energy of the bound complex. These were also subsequently predicted by the other three softwares—RNAhybrid, MicroInspector and DIANAMicro-T.

miRNA expression levels were monitored using a primer extension based protocol (see below) standardized for the purpose. As shown in FIG. 4, the miRNA expression levels could be detected by monitoring a radioactively labeled anti-miRNA probe in a sequence dependent manner (FIG. 4). Expression levels of miRNAs 29a and 29b which showed anti-nef activity were expressed at different levels in different control individuals.

Detection of miRNA Using Primer Extension

The mixture of total RNA and double autoclaved water in the ratio 1:10 is heated in a boiling water bath for 5-10 minutes followed by chilling in ice for the same duration. Subsequently, it is kept at room temperature for 10-15 minutes followed by addition of diluted dATP, dGTP and dTTP and 10×RT buffer. 1 µl of α-P-32-dCTP was added after which RT enzyme is added. The reaction mix was then incubated at 37° C. for 30 min. The reaction was stopped by adding 2 µl 1N NaOH and 0.5 µl 0.5 M EDTA and the sample was incubated at 65° C. for 30 min. After 30 min 7 µl 1M Tris-HCl (pH 7.5) was added to the mixture. The samples were prepared as explained below and run on 18% polyacrylamide gel containing urea (8M).

Sample Preparation: 16 M Urea was added to the samples to make the final conc. of urea to 8M. The samples were then heated at 65° C. for 5-10 min, mixed with loading dye and loaded in 18% urea-containing PAGE. After running, the gel was kept in fixing solution (10% Methanol, 10% Glacial Acetic Acid) for 1 hr on a rocker. After fixing, the gel was washed with water twice, wrapped in Saran Wrap and was put for exposure. The image was scanned after overnight exposure.

Luciferase Assay:

Preparation of Lysate:

Lysate is prepared by suspending HeLa cells in 5× lysis buffer (CCLR, RLB or PLB) after removal of the growth medium by rinsing with PBS buffer followed by freeze thaw. The suspension is centrifuged at 12,000×g for 15 seconds at room temperature followed by centrifugation at 4 degree centigrade for 2 minutes. The supernatant (cell lysate) is stored at minus 70 degree centigrade.

Luciferase Assay using Luminometer:

Dispense 100 µl of the Luciferase Assay Reagent into luminometer tubes, one tube per sample. Program the luminometer to perform a 2-second measurement delay followed by a 10-second measurement read for luciferase activity. The read time may be shortened if sufficient light is produced. Add 20 µl of cell lysate to a luminometer tube containing the Luciferase Assay Reagent. Mix by pipetting 2.3 times or vortex briefly. Place the tube in the luminometer and initiate reading.

Mapping of miRNA Targets:

The miRNAs hsa-mir-29a, hsa-mir-29b and hsa-mir-29c target the nef gene whereas hsa-mir-149, hsa-mir-324-5p and hsa-mir-378 target vpr, vif and env respectively. nef, vpr and vif are accessory genes of HIV-1 which are required for HIV-1 infection. The Nef protein is involved in both replication and pathogenesis of HIV-1. It has been established that Nef enhances Tat mediated gene expression from the LTR by activating signaling pathways as a consequence of which there is an increase in the activation of general transcription factors as well as the translocation of repression factors from the nucleus. The Vpr protein is involved in a range of functions which include induction of cell cycle arrest in the G(2) phase, transactivation of the viral promoter, nuclear import of preintegration complexes, and induction of apoptosis in the infected cell. The Vif protein is understood to play an important role during viral assembly in producer cells to ensure infectivity in infected cells. The env gene product is Envelope surface glycoprotein which is important in entry of the HIV to the cell. Entry of HIV into target cells requires sequential interactions of the viral envelope protein (Env) with CD4 and appropriate chemokine receptor on the target cell.

Comparison of Target Sequences in Related HIV-1 Strains:

The variability of viral genomes can pose a problem in using RNA interference. Therefore we compared the sequence conservation at the target site amongst different HIV-1 clades. It was observed that the target regions were significantly conserved. The genes to which the target regions belong varied among some of the strains, mostly in the Clade O. However, the clade O is known to be a highly polymorphic strain when compared to the other sub-groups M and N.

Expression Variation Studies:

Recently microarray experiments have been used to generate data on tissue and cell type specific expression profiles of microRNAs. MicroRNAs can be effective anti-viral regulatory strategies of host cells only if the microRNA is expressed at the site of infection by the virus. Probes for hsa-mir-29c, hsa-mir-378 and hsa-mir-324-5p were not available on the arrays. Expression data reported from previous studies show that the miRNAs hsa-mir-29a, hsa-mir-29b and hsa-mir-149 are expressed in T cells.

There have been reports of defective accessory genes being a probable cause of delayed response to HIV-1 infection. nef gene function loss has been, arguably, reported to play an important role in disease progression. Individuals who do not develop Acquired Immuno Deficiency Syndrome (AIDS) even several years after infection have been shown to harbour defective or non-functional genes in the viral genome. Polymorphisms in miRNA sequences that target the HIV-1 or variation in the expression levels of these miRNAs between individuals, hence, may also contribute to disease progression. However, neither published literature nor database entries report polymorphisms in the mature miRNAs that target HIV-1 as well as in their respective pre-miRNA sequences. The inventors used recently reported microarray based miRNA expression profiles to identify the expression pattern of the five miRNAs which target the HIV-1 genes. The raw expression values were retrieved and re-normalised. The data from all experiments was scaled to enable comparison.

The scaled and normalized expression levels of the microRNAs in 73 samples were calculated. In addition hsa-mir-29a and hsa-mir-29b miRNAs expressed in T-cells can repress nef function and thus influence disease progression. nef is also known to be regulated by a HIV-1 miRNA. HIV-1 strains from long-term non-progressors have been shown to harbor defective nef genes. The limited amount of expression data currently available implies that these miRNAs show variable levels of expression in different samples. Study of the expression levels of these miRNAs, in normal individuals and infected individuals who do not develop disease after prolonged periods of infection can, in future, reveal the role of human miRNA expression in accounting for differences in disease progression.

Another aspect of the invention is associating variations in expression levels of miRNA with progression of disease. This is carried out by microarray experiments and other high throughput primer extension based methods wherein miRNA expression levels are detected in patients and control individuals. The expression levels of miRNAs may provide prognostic information about HIV progression.

Use of Chemically Modified miRNAs to Target HIV:

Another aspect of the invention is targeting HIV genes using chemically modified synthetic oligomers that act as miRNAs.

The following examples are given by way of illustration of the present invention and therefore should not be construed to limit the scope of the present invention

EXAMPLE 1

Data Retrieval

The human microRNA mature sequences were downloaded from the database of miRNA maintained by the Sanger Center named—The miRNA Registry at the Sanger Institute website. The entire list of miRNA that were downloaded is given as Table 1. For querying probable targets in the HIV-1 genome, the inventors used the RefSeq validated HIV-1 reference sequence, obtained from the NCBI website and 12 representative related strain sequences, as identified by the International Committee on Taxonomy of Viruses (ICTV). The Glade sequences were obtained from ICTV database. The accession numbers of the clades are given in Table 2.

EXAMPLE 2

Prediction of miRNA Targets in HIV-1

Four well-established microRNA target prediction softwares—miRanda, RNAhybrid, MicroInspector and DIANA-MicroT were used to predict targets for the 211 human miRNAs in the HIV-1 reference sequence and the 12 representative lade sequences. HIV-1 targets to human microRNAs were initially predicted using miRanda with default parameters (Gap Open Penalty: −8.0; Gap Extend: −2.0; Score Threshold: 50.0; Energy Threshold: −20.0 kcal/mol; Scaling Parameter: 2.0). In order to increase the stringency, a cut-off score was derived above which the miRNA-target pairs were selected. The cut-off score of 120 was derived by running the same program on a shuffled sequence of HIV-1 reference strain with the same set of miRNAs. HIV-1 genome sequence was shuffled using the EMBOSS2 program shuffleseq. This enabled filtering of probable false positive hits and selection of the most probable and high-scoring values. These short-listed HIV-1 targets to human microRNAs were also found to be highly probable targets on the other prediction software. The top scoring miRNA-target pairs are tabulated in Table 3. Prior to running the RNAhybrid program, the RNAcalibrate module was used to derive the xi and theta values for calculation of Extreme Value Distribution. The xi-theta values thus obtained were included as one of the parameters while using RNAhybrid for target prediction. This minimizes the base composition bias. Also, the helix parameters were set to include maximum continuous complementarity towards the 5' end of the miRNA. It was observed that out of the several probable targets predicted by RNAhybrid, the six filtered pairs from miRanda had the lowest minimum free energy. Similar observations were made when the other two software were employed with default parameters, viz., minimum free energy of −20. Similarly the targets were predicted on the representative clade sequences also using miRanda. The target regions were mapped to the genomes of the 12 HIV clades. The target sites for the respective miRNAs were aligned using TCoffee server.

Validation of miRNA Targets in HIV Genome:

The target of miRNA 29a, 29b and 29c found in the nef gene of HIV genome was further validated by experimental means. The validation was carried out in a cell culture model employing HeLa cells. Primer extension based methods described below were used to ensure that HeLa cells express the miRNAs being tested. A vector with the firefly luciferase gene under the control of a constitutive promoter was used to monitor the activity of the miRNA. Cultured HeLa cells were transfected with various constructs bearing reporter gene which carried testable target regions in their 3'Untranslated regions. Subsequently, the reporter gene activity was monitored using enzymatic assays. The expression level of the reporter would be expected to get down regulated if the cellular miRNA binds to the 3'UTR and results in translational block of the target HIV-1 gene (scheme 1). Furthermore, specificity of the interaction was validated by introducing an anti-miRNA, complimentary in sequence to the miRNA being tested. The DNA oligonucleotide which acts as an anti-miRNA molecule interferes in the action of the miRNA and restores the reporter gene activity.

Targets for 29a, and 29b within the nef gene showed dependence on the miRNA in the Hela cell since expression levels from the clone carrying the target region were downregulated compared to the expression from the vector without the target regions. Anti-miRNA against 29a and 29b could partially restore the reporter activity (FIG. 2 and FIG. 3). However an unrelated anti-miRNA i.e. anti-mir 149 had no such effect proving that this is not a non-specific effect of DNA oligos.

EXAMPLE 3

Mapping of miRNA Targets

The miRNAs hsa-mir-29a, hsa-mir-29b and hsa-mir-29c target the nef gene whereas hsa-mir-149, hsa-mir-324-5p and hsa-mir-378 target vpr, vif and env respectively. nef, vpr and vif are accessory genes of HIV-1. The Nef protein is involved in both replication and pathogenesis of HIV-1. It has been established that Nef enhances Tat mediated gene expression from the LTR by activating signaling pathways as a consequence of which there is an increase in the activation of general transcription factors as well as the translocation of repression factors from the nucleus. The Vpr protein is involved in a range of functions which include induction of cell cycle arrest in the G(2) phase, transactivation of the viral promoter, nuclear import of preintegration complexes, and induction of apoptosis in the infected cell. The Vif protein is understood to play an important role during viral assembly in producer cells to ensure infectivity in infected cells. The env gene product is Envelope surface glycoprotein which is important in entry of the HIV to the cell.

EXAMPLE 4

Comparison of Target Sequences in Related HIV-1 Strains

The variability of viral genomes can pose a problem in using RNA interference. Therefore we compared the sequence conservation at the target site amongst different HIV-1 clades. It was observed that the target regions were significantly conserved. The genes to which the target regions belong varied among some of the strains, mostly in the Clade O. However, the clade O is known to be a highly polymorphic strain when compared to the other sub-groups M and N. The genes which encompass the target regions are tabulated in Table 4.

EXAMPLE 5

Expression Profile Analysis of miRNA

Microarray based expression data was retrieved from ArrayExpress database. The raw intensity data for each experiment was log transformed and then used for the calculation of Z scores. Z scores were calculated by subtracting the overall average gene intensity (within a single experiment) from the raw intensity data for each gene, and dividing the result by the standard deviation of all of the measured intensities, according to the formula:

$$Z \text{ score} = (\text{Intensity } G\text{-mean intensity } G1 \ldots Gn)/SDG1 \ldots Gn.$$

The graph representing the varying levels of miRNA expression is shown in FIG. 2.

In addition hsa-mir-29a and hsa-mir-29b miRNAs expressed in T-cells can repress nef function and thus influence disease progression. nef is also known to be regulated by a HIV-1 miRNA. HIV-1 strains from long-term non-progressors have been shown to harbor defective nef genes. The limited amount of expression data currently available implies that these miRNAs show variable levels of expression in different samples. Study of the expression levels of these miRNAs, in normal individuals and infected individuals who do not develop disease after prolonged periods of infection can, in future, reveal the role of human miRNA expression in accounting for differences in disease progression.

Another aspect of the invention is associating variations in expression levels of miRNA with progression of disease. This is carried out by microarray experiments wherein miRNA expression levels are detected in patients and control individuals.

Detection of miRNA using Primer Extension Protocol

1. In an Eppendarf tube, 1 μg of total RNA and 1 μl of primer (10 pmole/μl) were taken and the final volume was made to 10 μl using double autoclaved water. Note: If the RNA is at a high conc. and had been stored at −20° C. for long, then warm the RNA before use.

2. The mixture was heated in a boiling water bath for 5-10 min and then chilled in ice for 5-10 min. The tube was then kept at room temperature. for 10-15 min.

3. dATP, dGTP and dTTP were diluted 5 times from their stock of 2 mM each. 2 μl of each of them was then added to the reaction mixture. 10×RT Buffer was also added. Then 1 μl of α-P-32-dCTP was added to the reaction mixture and finally RT enzyme was added. The reaction mix was then incubated at 37° C. for 30 min.

4. The reaction was stopped by adding 2 μl 1N NaOH and 0.5 μl 0.5M EDTA and the sample was incubated at 65° C. for 30 min. After 30 min 7 μl 1M Tris-HCl (pH 7.5) was added to the mixture.

5. The samples were prepared as explained below and run on 18% polyacrylamide gel containing urea (8M).

6. Sample Preparation: 16 M Urea was added to the samples to make the final conc. of urea to 8 M. The samples were then heated at 65° C. for 5-10 min, mixed with loading dye and loaded in 18% urea-containing PAGE. Note: Wash the wells properly before loading the samples.

7. After running, the gel was kept in fixing solution (10% Methanol, 10% Glacial Acetic Acid) for 1 hr on a rocker.

8. After fixing, the gel was washed with water twice, wrapped in Saran Wrap and was put for exposure.

9. The image was scanned after overnight exposure.

Luciferase Assay Protocol:

Preparation of Lysate:

1. Add 4 volumes of water to 1 volume of 5× lysis buffer. Equilibrate 1× lysis buffer to room temperature before use.

2. Carefully remove the growth medium from cells to be assayed. Rinse cells with PBS, being careful to not dislodge attached cells. Remove as much of the PBS rinse as possible.

3. Add enough 1× lysis buffer (CCLR, RLB or PLB) to cover the cells (e.g., 400 μl/60 mm culture dish, 900 μl/100 mm culture dish or 20 μl per well of a 96-well plate). If using RLB, perform a single freeze-thaw to ensure complete lysis.

4. Rock culture dishes several times to ensure complete coverage of the cells with lysis buffer. Scrape attached cells from the dish. Transfer cells and all liquid to a microcentrifuge tube. Place the tube on ice.

5. Vortex the microcentrifuge tube 10.15 seconds, then centrifuge at 12,000×g for 15 seconds (at room temperature) or up to 2 minutes (at 4° C.). Transfer the supernatant to a new tube.

6. Store the supernatant/cell lysate at 70° C.

Luciferase Assay Using Luminometer:

1. Dispense 100 μl of the Luciferase Assay Reagent into luminometer tubes, one tube per sample.

2. Program the luminometer to perform a 2-second measurement delay followed by a 10-second measurement read for luciferase activity. The read time may be shortened if sufficient light is produced.

Note: When using shorter assay times, validate the luminometer over that time period to ensure that readings are taken at a flat portion of the signal curve.

3. Add 20 μl of cell lysate to a luminometer tube containing the Luciferase Assay Reagent. Mix by pipetting 2.3 times or vortex briefly.

4. Place the tube in the luminometer and initiate reading.

EXAMPLE 6

Use of Chemically Modified miRNAs to Target HIV

Another aspect of the invention is targeting HIV genes using chemically modified synthetic oligomers that act as miRNAs. The nucleosides of the oligomer can be modified using strategies like Locked Nucleic Acid (LNA) or 2'-O-methyl RNA (OMe) resulting in better stability and binding to the target mRNA strand, thus enabling the repression of the HIV-1 proteins.

Advantages:

1. The main advantage of the invention is to provide a novel strategy to target genes of HIV-1 by human microRNAs, or its homologues, to inactivate or block HIV activity and obviate the drawbacks mentioned above.

2. Another advantage is to use synthetic miRNA, based on modified nucleosides, as therapeutic to prevent or inhibit the progression of disease.

3. Still another advantage is to provide miRNA expression variation as a genetic basis for long term progression of HIV infection.

4. Another advantage is to provide miRNA mediated inhibition of protein synthesis in HIV-1.

5. Yet another advantage of the invention is to use variation of expression of human miRNAs as a prognostic genetic bio-marker in HIV-1 infection.

TABLE 1

The 211 human microRNAs used in the analyses.
Nomenclature as per the microRNA Registry hsa-let-7a
hsa-let-7b
hsa-let-7c
hsa-let-7d
hsa-let-7e
hsa-let-7f
hsa-let-7g
hsa-let-7i
hsa-miR-1
hsa-miR-100
hsa-miR-101
hsa-miR-103
hsa-miR-105
hsa-miR-106a
hsa-miR-106b
hsa-miR-107
hsa-miR-10a
hsa-miR-10b
hsa-miR-122a
hsa-miR-124a
hsa-miR-125a
hsa-miR-125b
hsa-miR-126
hsa-miR-126*
hsa-miR-127
hsa-miR-128a
hsa-miR-128b
hsa-miR-129
hsa-miR-130a
hsa-miR-130b
hsa-miR-132
hsa-miR-133a
hsa-miR-133b
hsa-miR-134
hsa-miR-135a
hsa-miR-135b
hsa-miR-136
hsa-miR-137
hsa-miR-138
hsa-miR-139
hsa-miR-140
hsa-miR-141
hsa-miR-142-3p
hsa-miR-142-5p
hsa-miR-143
hsa-miR-144
hsa-miR-145
hsa-miR-146
hsa-miR-147
hsa-miR-148a
hsa-miR-148b
hsa-miR-149
hsa-miR-150
hsa-miR-151
hsa-miR-152
hsa-miR-153

TABLE 1-continued

The 211 human microRNAs used in the analyses.
Nomenclature as per the microRNA Registry hsa-miR-154
hsa-miR-154*
hsa-miR-155
hsa-miR-15a
hsa-miR-15b
hsa-miR-16
hsa-miR-17-3p
hsa-miR-17-5p
hsa-miR-18
hsa-miR-181a
hsa-miR-181b
hsa-miR-181c
hsa-miR-182
hsa-miR-182*
hsa-miR-183
hsa-miR-184
hsa-miR-185
hsa-miR-186
hsa-miR-187
hsa-miR-188
hsa-miR-189
hsa-miR-190
hsa-miR-191
hsa-miR-192
hsa-miR-193
hsa-miR-194
hsa-miR-195
hsa-miR-196a
hsa-miR-196b
hsa-miR-197
hsa-miR-198
hsa-miR-199a
hsa-miR-199a*
hsa-miR-199b
hsa-miR-19a
hsa-miR-19b
hsa-miR-20
hsa-miR-200a
hsa-miR-200b
hsa-miR-200c
hsa-miR-203
hsa-miR-204
hsa-miR-205
hsa-miR-206
hsa-miR-208
hsa-miR-21
hsa-miR-210
hsa-miR-211
hsa-miR-212
hsa-miR-213
hsa-miR-214
hsa-miR-215
hsa-miR-216
hsa-miR-217
hsa-miR-218
hsa-miR-219
hsa-miR-22
hsa-miR-220
hsa-miR-221
hsa-miR-222
hsa-miR-223
hsa-miR-224
hsa-miR-23a
hsa-miR-23b
hsa-miR-24
hsa-miR-25
hsa-miR-26a
hsa-miR-26b
hsa-miR-27a
hsa-miR-27b
hsa-miR-28
hsa-miR-296
hsa-miR-299
hsa-miR-29a
hsa-miR-29b
hsa-miR-29c TABLE 1-continued The 211 human microRNAs used in the analyses.
Nomenclature as per the microRNA Registry hsa-miR-301
hsa-miR-302a
hsa-miR-302a*
hsa-miR-302b
hsa-miR-302b*
hsa-miR-302c
hsa-miR-302c*
hsa-miR-302d
hsa-miR-30a-3p
hsa-miR-30a-5p
hsa-miR-30b
hsa-miR-30c
hsa-miR-30d
hsa-miR-30e-3p
hsa-miR-30e-5p
hsa-miR-31
hsa-miR-32
hsa-miR-320
hsa-miR-323
hsa-miR-324-3p
hsa-miR-324-5p
hsa-miR-325
hsa-miR-326
hsa-miR-328
hsa-miR-33
hsa-miR-330
hsa-miR-331
hsa-miR-335
hsa-miR-337
hsa-miR-338
hsa-miR-339
hsa-miR-340
hsa-miR-342
hsa-miR-345
hsa-miR-346
hsa-miR-34a
hsa-miR-34b
hsa-miR-34c
hsa-miR-361
hsa-miR-365
hsa-miR-367
hsa-miR-368
hsa-miR-369
hsa-miR-370
hsa-miR-371
hsa-miR-372
hsa-miR-373
hsa-miR-373*
hsa-miR-374
hsa-miR-375
hsa-miR-376a
hsa-miR-377
hsa-miR-378
hsa-miR-379
hsa-miR-380-3p
hsa-miR-380-5p
hsa-miR-381
hsa-miR-382
hsa-miR-383
hsa-miR-384
hsa-miR-422a
hsa-miR-422b
hsa-miR-423
hsa-miR-424
hsa-miR-425
hsa-miR-429
hsa-miR-448
hsa-miR-449
hsa-miR-450
hsa-miR-7
hsa-miR-9
hsa-miR-9*
hsa-miR-92

TABLE 1-continued

The 211 human microRNAs used in the analyses.
Nomenclature as per the microRNA Registry hsa-miR-93
hsa-miR-95
hsa-miR-96
hsa-miR-98
hsa-miR-99a
hsa-miR-99b

TABLE 2

Details of the HIV-1 clades.

| Description | Reference strain | Accession |
|---|---|---|
| Clade A | 00.061.1.06.009.05.001.011 | U455 [M62320] |
| Clade B | 00.061.1.06.009.05.001.001 | ARV-2/SF-2 [K02007] |
| Clade B | 00.061.1.06.009.05.001.002 | BRU (LAI) [K02013] |
| Clade B | 00.061.1.06.009.05.001.003 | CAM1 [D10112] |
| Clade B | 00.061.1.06.009.05.001.004 | ELI [X04414] |
| Clade B | 00.061.1.06.009.05.001.005 | HXB2 [K03455] |
| Clade C | 00.061.1.06.009.05.003.013 | ETH2220 [U46016] |
| Clade D | 00.061.1.06.009.05.001.008 | NDK [M27323] |
| Clade D | 00.061.1.06.009.05.004.004 | ELI [X004414.K03454] |
| Clade F | 00.061.1.06.009.05.005.014 | 93BR020 [AF005494] |
| Clade H | 00.061.1.06.009.05.006.015 | 90CR056 [AF005496] |
| Clade O | 00.061.1.06.009.05.007.016 | ANT70 [L20587] |

TABLE 3

Top scoring miRNA-target pairs.

| Human microRNA | Mature miRNA sequence | Start position of target binding |
|---|---|---|
| hsa-miR-29a | 3' UUGGCU-AAAGUCUACCACGAU 5'<br>      \|:\|\|  \|\|:\|\|\|\|\|\|\|\|\|\|\|<br>5' CACTGACCTTTGGATGGTCTA 3' | (SEQ ID NO: 7)<br>8749<br>(SEQ ID NO: 1) |
| hsa-miR-29b | 3' UUGUGACU-AAAGUUUACCACGAU 5'<br>   \|\|\|\|\|\|  \|\|:\|\|\|\|\|\|\|\|\|\|\|<br>5' TCCACTGACCTTTGGATGGTCTA 3' | (SEQ ID NO: 8)<br>8749<br>(SEQ ID NO: 2) |
| hsa-miR-29c | 3' UGGCU-AAAGUUUACCACGAU 5'<br>   \|:\|\|  \|\|:\|\|\|\|\|\|\|\|\|\|\|<br>5' ACTGACCTTTGGATGGTCTA 3' | (SEQ ID NO: 9)<br>8749<br>(SEQ ID NO: 3) |
| hsa-miR-149 | 3' CCUCAC-UUCUGUGCCUCGGUCU 5'<br>  \|\|\|\| \|  \|\|\|\| \|\|\|\|\|\|\|\|\|\|\|<br>5' GGAGAGCAAGAAATGGAGCCAGT 3' | (SEQ ID NO: 10)<br>5364<br>(SEQ ID NO: 4) |
| hsa-miR-324-5p | 3' UGUGGUUACGG-GAUCCCCUACGC 5'<br>  ::\|\|  \|\| \|\| \|\|\|\|\|\|\|\|\|\|<br>5' GTACACATCCCACTAGGGGATGCT 3' | (SEQ ID NO: 11)<br>4748<br>(SEQ ID NO: 5) |
| hsa-miR-378 | 3' UGUGUCCUGGACCUCAGUCCUC 5'<br>  :\|\|\|\|   :\|\|\|\|\|\|\|\|\|\|\|<br>5' CTACAGTA-TTGGAGTCAGGAA 3' | (SEQ ID NO: 12)<br>8168<br>(SEQ ID NO: 6) |

TABLE 4

Genes encompassing target regions in the HIV-1 clades:

| | HIV-1 reference sequence | clade A: M62320.1 | clade B: K02007.1 | clade B: K02013.1 | clade B: K03455.1 | clade B: M17451.1 | clade B: M17449.1 |
|---|---|---|---|---|---|---|---|
| hsa-miR-29b | nef | nef | — | nef | — | nef | — |
| hsa-miR-29a | nef | nef | — | nef | — | nef | — |
| hsa-miR-29c | nef | nef | — | nef | — | nef | — |
| hsa-miR-149 | vpr | vpr | vpr | vpr | — | vpr | vpr |
| hsa-miR-378 | env | pol | env | env | env | rev/env | env |
| hsa-miR-324-5p | vif | vif | vif | vif | sor | tat/rev/env | vif |

| | clade C: U46016.1 | Clade D: M27323.1 | clade D: K03454.1 | clade F: AF005494.1 | clade H: AF005496.1 | Clade O: L20587.1 |
|---|---|---|---|---|---|---|
| hsa-miR-29b | nef | nef | nef | nef | nef | — |
| hsa-miR-29a | nef | nef | nef | nef | nef | — |
| hsa-miR-29c | nef | nef | nef | nef | nef | — |
| hsa-miR-149 | vpr | tat/rev | tat/rev | tat/rev | tat/rev | vpr |
| hsa-miR-378 | Gp 160 | rev/env | rev/env | env/rev | tat/rev/env | vif |
| hsa-miR-324-5p | pol | vpr | gag | gag-pol | gag-pol | — |

Primer Sequences
29a_I_L . . . AACCGATTTCAGAT - (SEQ ID NO: 13)
29b1_I_L . . . CACTGATTTCAAATGG - (SEQ ID NO: 14)
29c_I_L . . . CCGATTTCAAATGGTG - (SEQ ID NO: 15)

What is claimed is:

1. An isolated human miRNA target nucleic acid from a HIV genome consisting of a nucleotide sequence consisting of SEQ ID NO: 1 or 16.

2. An isolated nucleic acid consisting of the reverse complement of a nucleotide sequence consisting of SEQ ID NO: 1 or 16.

* * * * *